(12) United States Patent
Pyun

(10) Patent No.: US 11,761,957 B2
(45) Date of Patent: Sep. 19, 2023

(54) BIO-ELECTRODE, CHRONOAMPEROMETRY DEVICE, IMMUNOASSAY DEVICE AND METHOD USING THE SAME

(71) Applicant: UNIVERSITY—INDUSTRY FOUNDATION(UIF), YONSEI UNIVER, Seoul (KR)

(72) Inventor: Jae-Chul Pyun, Seoul (KR)

(73) Assignee: UNIVERSITY—INDUSTRY FOUNDATION (UIF), YONSEI UNIVERSITY, Seoul (KR)

( * ) Notice: Subject to any disclaimer, the term of this patent is extended or adjusted under 35 U.S.C. 154(b) by 598 days.

(21) Appl. No.: 16/833,602

(22) Filed: Mar. 29, 2020

(65) Prior Publication Data

US 2020/0378960 A1 Dec. 3, 2020

(51) Int. Cl.
| | |
|---|---|
| *G01N 33/543* | (2006.01) |
| *G01N 27/327* | (2006.01) |
| *H01M 4/1395* | (2010.01) |
| *C01G 49/00* | (2006.01) |
| *C01G 7/00* | (2006.01) |
| *C07C 267/00* | (2006.01) |

(Continued)

(52) U.S. Cl.
CPC ......... *G01N 33/5438* (2013.01); *C01F 17/00* (2013.01); *C01G 7/00* (2013.01); *C01G 49/00* (2013.01); *C07C 267/00* (2013.01); *G01N 27/3278* (2013.01); *H01M 4/1395* (2013.01); *B82Y 40/00* (2013.01); *C01P 2004/64* (2013.01); *C07C 2601/16* (2017.05); *H01M 2004/021* (2013.01)

(58) Field of Classification Search
CPC .......... G01N 33/5438; G01N 27/3278; G01N 27/4161; G01N 27/3271; G01N 27/3272; G01N 27/49; G01N 27/3277; C01F 17/00; C01G 7/00; C01G 49/00; C07C 267/00; C07C 2601/16; H01M 4/1395; H01M 2004/021; Y02E 60/10; B82Y 40/00; C01P 2004/64
See application file for complete search history.

(56) References Cited

FOREIGN PATENT DOCUMENTS

| KR | 10-2005-0090285 | 5/2006 |
|---|---|---|
| KR | 10-2016-0004421 | 8/2016 |

OTHER PUBLICATIONS

M. Sachsenhauser, et al., "Surface State Mediated Electron Transfer Across the N-Type SiC/Electrolyte Interface", Journal of Physical Chemistry C, 120(12): p. 6524-6533 (Year: 2016).*

(Continued)

*Primary Examiner* — J. Christopher Ball
(74) *Attorney, Agent, or Firm* — McLean IP Global; Jason Y. Pahng

(57) ABSTRACT

The present invention relates to a bio-electrode for current measurement including silicon carbide (SiC) doped at least partially with nitrogen (N). The bio-electrode for current measurement according to an embodiment of the present invention is a bio-electrode for a current measurement which is contact with an object to be analyzed, which generates a current signal by an electrochemical reaction, and includes silicon carbide (SiC) doped at least partially with nitrogen (N). The electrode may be used in a high-sensitive bio-quantification kit, a high-sensitive bio-quantification device, and an immunoassay device.

13 Claims, 10 Drawing Sheets

(51) Int. Cl.
*C01F 17/00* (2020.01)
*H01M 4/02* (2006.01)
*B82Y 40/00* (2011.01)

(56) References Cited

OTHER PUBLICATIONS

Korean Office Action for Application No. KR 10-2019-0037021 dated Aug. 29, 2020.

* cited by examiner

BIO-ELECTRODE, CHRONOAMPEROMETRY DEVICE, IMMUNOASSAY DEVICE AND METHOD USING THE SAME

CROSS-REFERENCES TO RELATED APPLICATION

The present application claims the benefit of Korean application number 10-2019-0037021, filed on Mar. 29, 2019, which is herein incorporated by reference in its entirety.

BACKGROUND OF THE INVENTION

1. Field

The present invention relates to a technology for detecting analytes, and more particularly, to a high-sensitive bio-quantification kit, a high-sensitive bio-quantification device, an immunoassay device, and method of analysis using the same.

2. Description of the Related Art

The immunoassay is a method of measuring the concentration of an analyte by using a specific coupling between an antigen and an antibody. In general, a method using the analyte as an antigen and an antibody specifically coupling to the analyte is used. After the antibody corresponding to the analyte is fixed on a solid support such as a plate or a bead, and when the sample containing the analyte is reacted with the antibody, the analyte may be bound to the fixed antibody. In order to measure the concentration of the analyte bound to the antibody, a secondary antibody capable of specifically coupling to the analyte is treated, and the secondary antibody is coupled to an enzyme capable of causing a chromophoric, fluorescent or luminescent reactions. Therefore, the intensity of color development or luminescence has a quantitatively proportional relationship with the concentration of the analyte.

In order to use the color development, fluorescence, or luminescence, a measuring device having an optical system is generally required. The measuring device having the optical system is a great barrier to miniaturization of a diagnostic device using an immunoassay.

In addition, it is possible to measure an analyte having an only concentration greater than a considerable level by an optical measurement method such as color development, fluorescence, and luminescence, and thus it is difficult to apply for diagnostic tests requiring high reliability, measurement limits, and measurement sensitivity.

SUMMARY OF THE INVENTION

The problem to be solved by the present invention is to provide a bio-electrode which improves reliability and measurement sensitivity, and enables miniaturization of diagnostic kits and devices.

In addition, the problem to be solved by the present invention is to provide a high-sensitive bio-quantification kit having improved measurement sensitivity and reliability which may detect very low concentrations of analytes.

Furthermore, it is to provide a chronoamperometry device for immunoassays that provides the above advantages, and to provide an immunoassay analysis method using the electrode and the chronoamperometry device.

In order to solve the above problems, the bio-electrode for current measurement according to the present invention is a bio-electrode for current measurement which is contacted with an analyte that generates a current signal by an electrochemical reaction, and includes silicon carbide(SiC) doped with nitrogen(N) in at least some portions of the bio-electrode. The doping concentration of nitrogen may be $4 \times 10^{18}/cm^3$ to $6 \times 10^{18}/cm^3$.

In some embodiments, the silicon carbide may have a crystal structure of 4H-SiC, and optionally, the oxidation-reduction potential window of the bio-electrode for current measurement may be −700 mV to 2500 mV. In addition, the surface capacitance of the silicon carbide may be 3.59 $\mu F/cm^2$ to 3.71 $\mu F/cm^2$.

A high-sensitive bio-quantification kit according to another embodiment of the present invention may comprise a substrate receiving an analyte and providing at least one or more electrochemical reaction regions; and a working electrode and a counter electrode arranged in the electrochemical reaction region to induce an electrochemical reaction of the analyte, and to detect a current change resulting from the electrochemical reaction. Further, at least one of the working electrode and the counter electrode may include silicon carbide doped at least partially with nitrogen.

In another embodiment, a high-sensitive bio-quantification device may comprise a working electrode and a counter electrode which are in contact with an analyte that generates a current signal by an electrochemical reaction, and includes silicon carbide doped at least partially with nitrogen; and a current measurer which induces an electrochemical reaction of the analyte by applying a driving voltage and measures a current generated by the electrochemical reaction. Optionally, the current measurer may use chronoamperometry.

In some embodiments, the chronoamperometry may sequentially apply the reduction potential voltage and the oxidation potential voltage of the analyte, and measure the current over time, and the chronoamperometry may generate a smaller background current than a case when measuring the current using cyclic voltammetry.

An immunoassay device according to another embodiment of the present invention may comprise, an immunoassayer for generating an analyte comprising at least one or more of a labeling substance, a first oxide, or a second oxide, wherein a primary probe substance is fixed on a substrate, and a target substance to be quantified is processed to specifically be bound to the fixed first probe substance, a second probe substance with a labeling substance attached thereto is processed to specifically be bound to an antibody, and a chromogenic substrate is oxidized due to a catalytic reaction of the labeling substance attached to the secondary probe substance; a current measurer for contacting a silicon carbide (SiC) electrode doped at least partially with nitrogen (N) to the analyte, and for measuring the current of the analyte by applying a constant voltage; and a concentration analyzer for analyzing a concentration of the target substance by using the measured current.

In some embodiments, the labeling substance may be horseradish peroxidase (HRP), and the chromogenic substrate may be 3,3',5,5'-tetramethylbenzidine (TMB). Optionally, the target substance may be an antibody of anti-human immunodeficiency virus (HIV) or an antigen of human hepatitis B surface antigen (hHBsAg).

An immunoassay method according to another embodiment may comprise a step of processing a target substance, and specifically coupling the processed target substance to a substrate to which a primary probe substance is bound; a step for forming a second intermediate product by processing a secondary probe substance wherein a labeling substance is attached to the first intermediate product; a step for generating a first oxide or a second oxide by oxidizing a chromogenic substrate according to a catalytic reaction of a labeling substance in the second intermediate product; a step for providing a silicon carbide(SiC) electrode doped with nitrogen(N) used for measuring a current signal arising from an electrochemical reaction between the chromogenic substrate, the first oxide and the second oxide; a step for contacting a silicon carbide(SiC) electrode doped with of nitrogen(N) to at least a portion of the first oxide or the second oxide, and for applying a constant voltage to measure a current signal of analyte; and a step for analyzing the concentration of the target substance using the measured current signal.

In some embodiments, the current signal measurement may use chronoamperometry. In addition, the chronoamperometry(chronoamperometry) may comprise a step of sequentially applying a reduction potential voltage and an oxidation potential voltage of the chromogenic substrate, a step for measuring the current over time, and a step for obtaining a result value from a difference between a current magnitude when the reduction potential voltage is applied, and a current magnitude when the oxidation potential voltage is applied.

In another embodiment, the labeling substance may be horseradish peroxidase (HRP), the chromogenic substrate may be 3,3',5,5'-tetramethylbenzidine (TMB), and a measurement limit of an optical density of the target substance measured at 450 nm may be greater than 0.37 and less than 0.042.

According to an embodiment of the present invention, a silicon carbide (SiC) electrode doped with nitrogen (N) has a low surface capacitance and a high electron transfer rate due to semiconductor characteristics. Therefore, the noise current generated when measuring a current signal by the electrochemical reaction of the analyte may be reduced. The electrode may be provided as a bio-electrode for current measurement having high measurement sensitivity, high reliability, and low measurement limits since the electrode has electrochemical stability that is not oxidized or reduced at a wide range of potentials.

In addition, a high-sensitivity bio-quantification kit and a high-sensitivity bio-quantification device having the above advantages may be provided by measuring a current signal generated from the electrochemical reaction of the analyte by using the electrode.

In addition, in the case of the high-sensitivity bio-quantification device that detects the electrochemical reaction of the analyte, it is possible to measure an extremely low concentration of the analyte, unlike the conventional immunoassay analysis using color development, luminescence, and fluorescence. Therefore, it is possible to provide an immunoassay analysis apparatus with improved measurement sensitivity and reliability, and an immunoassay method using the same.\

In addition, when using the method for detecting the electrochemical reaction of the analyte, it is possible to implement a simple and compact immunoassay analysis device since a measurement device having an optical system is unnecessary. Further, a high-reliability medical diagnostic device may be provided by using an anti-human immunodeficiency virus(HIV) antibody, or human hepatitis B surface antigen(hHBsAg) antigen which requires considerable measurement sensitivity, as a target substance.

DETAILED DESCRIPTION OF THE INVENTION

Figure 1:
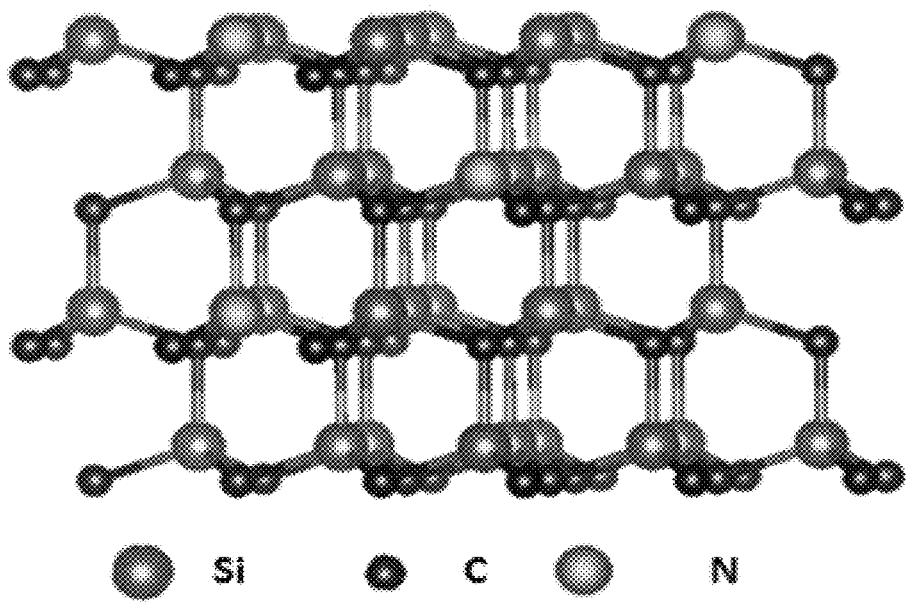
FIG. 1 is a structural diagram of a silicon carbide (SiC) electrode 10 doped with nitrogen (N) according to an embodiment of the present invention.

Hereinafter, the preferred embodiments of the present invention will be described in detail with reference to the accompanying drawings.

The embodiments of the present invention are provided to more completely describe the present invention to those having a common knowledge in the related art, and the following examples may be modified as various other forms, and the scope of the present invention is not limited to the following embodiments. Rather, these embodiments are provided to describe the present disclosure more faithfully and completely, and to fully convey the spirit of the present invention to those skilled in the art.

In addition, a thickness or a size of each layer in the drawings is exaggerated for convenience and clarity of description, and the same reference numerals in the drawings refer to the same elements. As used herein, the term, "and/or" includes any one, and all combinations of one or more of the listed items.

The terminology used herein is used to describe a specific embodiment and is not intended to limit the present invention. As used herein, the singular forms may include plural forms unless the context clearly indicates otherwise. Also, as used herein, the terms, "comprise" and/or "comprising" specifies the stated shapes, numbers, steps, actions, members, elements and/or the presence of these groups, and they do not exclude the presence or addition of one or more other shapes, numbers, actions, members, elements and/or, presence or addition of these groups.

Although the terms, "the first, the second, etc." are used herein to describe various members, components, regions, and/or parts, it is very apparent that these members, components, regions, and/or parts should not be limited by these terms. These terms are only used to distinguish one member, a component, a region or a part from another region or part. Accordingly, the first member, the first component, the first region or the first part described below may refer to the second member, the second component, the second region or the second part without departing from the teachings of the present invention.

Further, when one layer is formed or disposed on another layer, an intermediate layer may be formed or disposed between these layers. Similarly, even if one substance is adjacent to another, there may be an intermediate substance between these substances. Conversely, when a layer or a substance is said to be formed or disposed "directly" above or "directly" on another layer or substance, or when it is said to be "directly" or "directly adjacent" or in contact with another layer or substance, it should be understood that there are no intermediate substances or layers between these substances or layers.

Hereinafter, the embodiments of the present invention will be described with reference to the drawings schematically showing ideal embodiments of the present invention. In the drawings of the present invention, for example, a size and a shape of members may be exaggerated for convenience and clarity of description, and in actual implementation, the modified type of the illustrated shape may be expected. Accordingly, the embodiments of the present invention should not be construed as limited to the specific shapes of the regions shown herein.

Figure 2A:
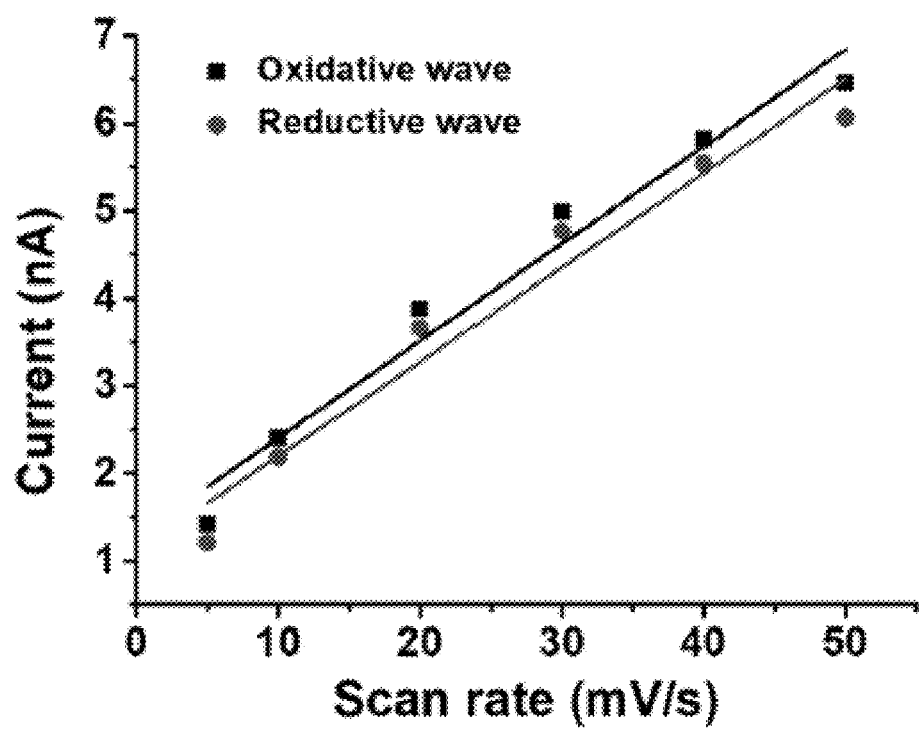
FIG. 2A is a graph showing a current change according to a potential change rate (Scan rate) applied to the electrode.
Figure 2B:
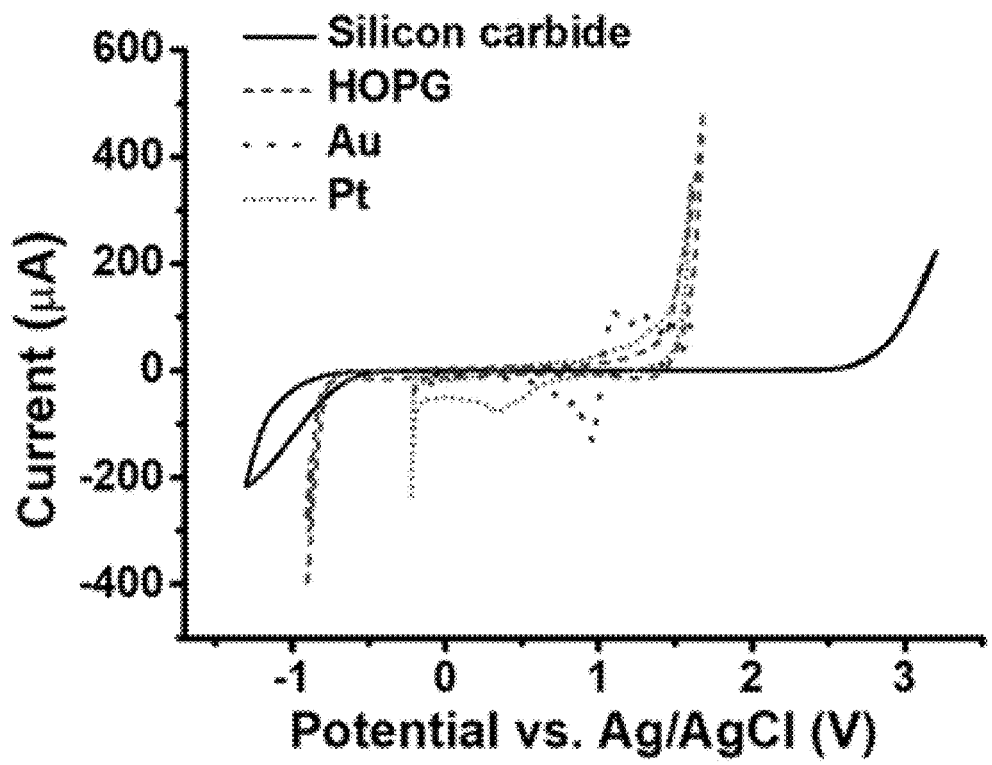
FIG. 2B is a graph showing the oxidation-reduction reaction window of the electrode, metal electrode, and carbon electrode.

FIG. 1 is a structural diagram of a silicon carbide (SiC) electrode 10 doped with nitrogen (N) according to an embodiment of the present invention, FIG. 2A is a graph showing a current change according to a potential change rate (scan rate) applied to the electrode 10, and FIG. 2B is a graph showing the oxidation-reduction reaction window of the electrode 10, metal electrode, and carbon electrode.

Referring to FIG. 1, in a silicon carbide (SiC) electrode according to an embodiment, nitrogen (N) is doped at a high concentration in a place of silicon (Si) in a silicon carbide (Si—C) crystal so that a part of the silicon (Si) may be substituted with the nitrogens. The electrode 10 may have conductive properties due to the non-covalent electron pair of nitrogen (N). In another embodiment, the doping concentration of nitrogen (N) may be $1 \times 10^{17}/cm^3$ to $9 \times 10^{19}/cm^3$, and the surface resistance of the electrode 10 is $0.1\Omega \times sq^{-1}$ to $10\Omega \times sq^{-1}$. In one embodiment, when the doping concentration of the nitrogen (N) is $5 \times 10^{18}/cm^3$, the surface resistance of the electrode 10 may be $0.4\Omega \times sq^{-1}$. When the doping concentration of the nitrogen (N) is less than $1 \times 10^{17}/cm^3$, it is difficult to obtain conductivity effective for the electrochemical analysis described later, and when the doping concentration of the nitrogen (N) exceeds $9 \times 10^{19}/cm^3$, oxidation and reduction of the electrode 10 itself occur within the operating voltage, making it difficult to derive a reliable result.

In one embodiment, the electrode 10 may have a crystal structure of 4H-SiC. When the silicon carbide (SiC) has a single crystal, more than 200 polytypes may be present. When it has a crystal structure of 4H-SiC, Raman analysis may show peaks of $1,518$ $cm^{-1}$ and $1,711$ $cm^{-1}$. In one embodiment, the electrode 10 may be provided by dividing the silicon wafer into a predetermined size through a cutting process after carbonization and nitrogen doping treatment. In another embodiment, it may be provided by subjecting the silicon carbide single crystal wafer to a nitrogen doping treatment and then dividing it into a predetermined size through the cutting process.

Referring to FIG. 2A, a current and a voltage satisfy the following equation.

$$I = C\left(\frac{dV}{dt}\right), I: \text{current, } C: \text{capacitance, } V: \text{voltage } t: \text{time}$$

Since FIG. 2 shows a change in current according to the rate of potential change, the slope of each graph in FIG. 2 may represent the surface capacitance of the silicon carbide (SiC) electrode. The graph may be obtained from results measured using cyclic voltammetry, and the surface capacitance may be measured by an oxidation reaction or a reduction reaction of the electrode 10, respectively. For example, a value of 3.71 $\mu F/cm^2$ may be measured by the oxidation reaction and 3.59 $\mu F/cm^2$ may be measured by the reduction reaction. Considering that 30.9 $\mu F/cm^2$ is measured for gold (Au), 64.2 $\mu F/cm^2$ is measured for platinum (Pt), 52.8 $\mu F/cm^2$ is measured for silver (Ag), and 39.8 $\mu F/cm^2$ is measured for stainless steel, the electrode 10 shows a very low value than the surface capacitance of the metal electrode. Further, when compared to 1~5 $\mu F/cm^2$ measured in the case of high-oriented pyrolytic graphite (HOPG) which is a carbon-based electrode, and 3.45 $\mu F/cm^2$ measured in diamond-like-carbon (DLC), it is understood that the similar values are obtained. When the surface capacitance is low, the noise voltage may be reduced by reducing the background voltage during I-V measurement for the detection of the analyte by electrochemical reaction, and accordingly, it is possible to measure a current sensitively.

Referring to FIG. 2B, it can be seen that the electrode 10 has an oxidation-reduction potential window ranging from −700 mV to 2,500 mV. In contrast, metal and carbon electrodes (HOPG) have a narrower range of potential window. In measuring the concentration of the analyte, the electrochemical reaction of the analyte means an oxidation-reduction reaction. If the oxidation-reduction reaction of the electrode itself occurs as well as in the analyte, the current signal generated in the oxidation-reduction reaction of the electrode itself overlaps with the current signal of the oxidation-reduction reaction of the analyte, thereby making accurate analysis difficult. In the present invention, as the oxidation-reduction reaction of the electrode itself does not occur, a potential range having measurement reliability is referred to as an oxidation-reduction potential window, and as the oxidation-reduction potential range is getting wider and wider, various types of compounds may be analyzed.

Figure 3:
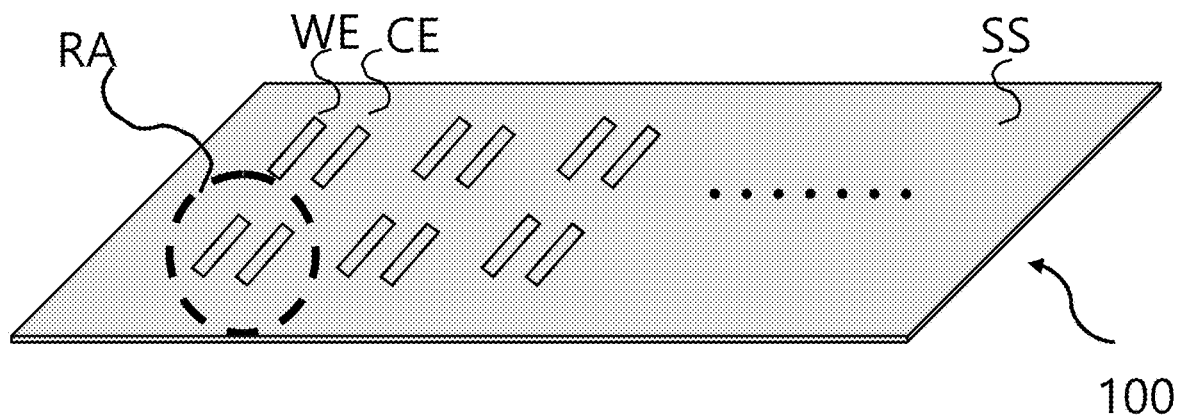
FIG. 3 is a structural diagram of a high-sensitive bio-quantification kit including an electrode.

FIG. 3 is a structural diagram of a high-sensitive bioquantification kit 100 including an electrode 10.

Referring to FIG. 3, in one embodiment, the high-sensitivity bio-quantification kit 100 may include a substrate SS, a working electrode WE and a counter electrode CE, and the working electrode WE may partially include a silicon carbide (SiC) doped with nitrogen (N) in at least some portions of the silicon carbide (SiC). In another embodiment, the counter electrode CE may also include silicon carbide (SiC) doped at least partially with nitrogen(N).

In one embodiment, the substrate SS accommodates the analyte and provides at least one or more electrochemical reaction region (RA in FIG. 3). The electrochemical reaction region may include an independent well which is suitably partitioned to accommodate a solution containing the analyte, and/or a conduit through which the analyte is supplied for realizing continuous measurement, and the present invention is not limited thereto.

In one embodiment, the electrochemical reaction region (RA in FIG. 3) may be provided in an array form as illustrated in FIG. 3. As a non-limiting example, a solution containing an analyte may be dropped into the electrochemical reaction region (RA in FIG. 3) or continuously supplied at a predetermined flow rate to the reaction region. Since the substrate SS detects the analyte by an electrochemical method, it is preferable that it is a nonconductor or a semiconductor, and does not require an optically transparent, opaque or translucent substance.

The working electrode WE and the counter electrode CE may be disposed in the electrochemical reaction region (RA in FIG. 3) to induce an electrochemical reaction of the analyte, and to detect a current change resulting from the electrochemical reaction. In one embodiment, the working electrode WE or the counter electrode CE may have a pad shape. In one embodiment, the high-sensitive bio-quantification kit 100 may include a reference electrode or an auxiliary electrode in addition to the working electrode WE and the counter electrode CE. Since the reference electrode has a constant electric potential, it may be an absolute reference of the potential measured using the high-sensitive bio-quantification kit 100. In addition, in another embodiment, since the high-sensitive bio-quantification kit 100 uses the electrodes as one unit, several of the units may be arranged in an array format, and the number of units is not limited.

Figure 4:
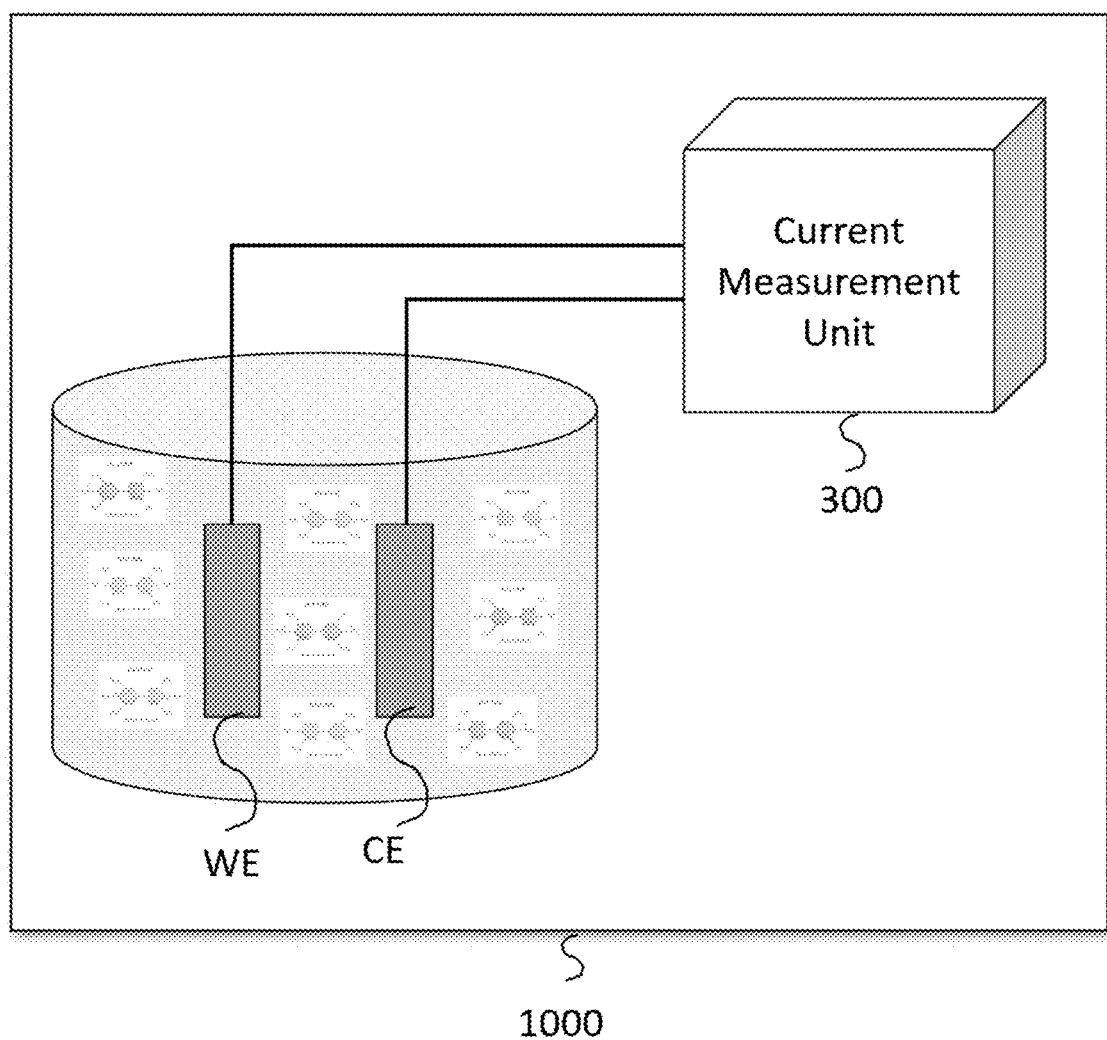
FIG. 4 is a structural diagram of a high-sensitive bio-quantification device 1000 including an electrode.

FIG. 4 is a structural diagram of a high-sensitive bio-quantification device 1000 including an electrode 10.

Referring to FIG. 4, in one embodiment, the high-sensitive bio-quantification device 1000 may include a working electrode WE, a counter electrode CE, and a current measurer 300. Descriptions of the working electrode WE and the counter electrode CE may refer to the abovementioned disclosure if there are no inconsistencies.

The current measurer 300 may induce an electrochemical reaction of the analyte by applying a driving voltage and may measure a current generated by the electrochemical reaction. The current measurer may include a working electrode WE or a counter electrode CE. In one embodiment, at least a portion of the working electrode WE or the counter electrode CE may contact the analyte. In one embodiment, the current measurer 300 may further include the reference electrode or the auxiliary electrode.

The working electrode WE, the counter electrode CE, or the reference electrode and the auxiliary electrode may be provided in the form of a probe to facilitate contact by an immersion method in a solution containing an analyte, and the present invention is not limited thereto. Also, the working electrode WE, the counter electrode CE, or the reference electrode and the auxiliary electrode may be arranged in an array form. In one example, the working electrode WE, the counter electrode CE, or the reference electrode and the auxiliary electrode may be fixed to a drive system movable in a horizontal or vertical direction, and therefore they may perform physical motions required for measurement.

In another embodiment, the current measurer 300 may be driven by using chronoamperometry. The chronoamperometry changes the voltage applied to the analyte over time and measures the magnitude of the current flowing through the analyte as the applied voltage is changed. In this embodiment, the reduction potential voltage and the oxidation potential voltage of the analyte may be sequentially applied between the working electrode WE and the counter electrode CE, and the current may be measured over time. For example, when the analyte is 3,3',5,5'-tetramethylbenzidine (TMB), the reduction potential voltage may be +600 mV, and the oxidation potential voltage may be −100 mV.

Figure 5:
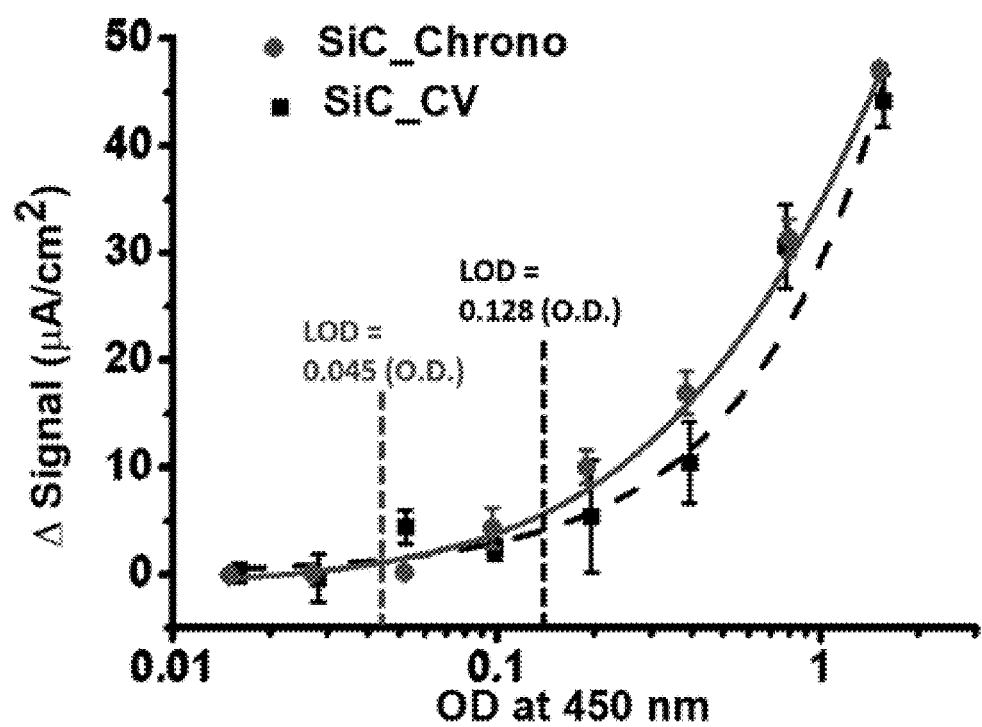
FIG. 5 is a graph measuring the current according to the chronoamperometry and the cyclic voltammetry according to an embodiment of the present invention.

In another embodiment, the chronoamperometry may generate a smaller background current than a case when measuring the current using cyclic voltammetry. The background current adversely affects the measurement sensitivity of concentration measurement of the analyte since it acts as a noise current. FIG. 5 is a graph measuring the current according to the chronoamperometry and the cyclic voltammetry according to an embodiment of the present invention. Referring to FIG. 5, it can be seen that a limit of detection (LOD) is lowered when measured by the chronoamperometry.

Figure 6:
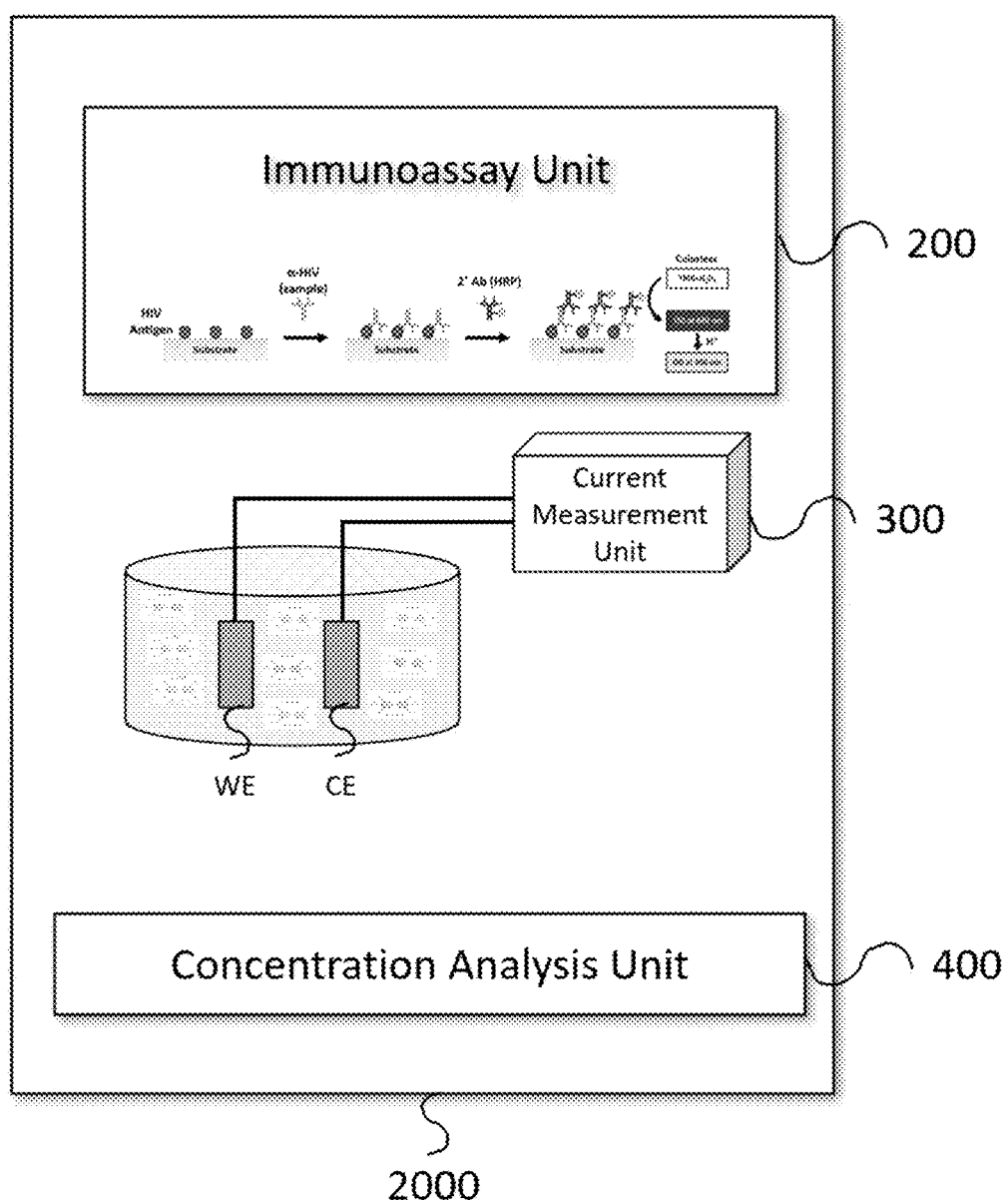
FIG. 6 is a diagram illustrating an immunoassay apparatus including a silicon carbide (SiC) electrode.

FIG. 6 is a diagram illustrating an immunoassay apparatus 2000 including a silicon carbide (SiC) electrode 10.

Referring to FIG. 6, the immunoassay apparatus 2000 may include an immunoassayer 200, a current measurer 300, and a concentration analyzer 400. The present invention is not limited to the above components, and may further include other components.

The immunoassayer 200 may fix a primary probe substance to the substrate, processes a target substance to be quantified, specifically couples the processed target substance to the primary probe substance, and specifically couples a secondary probe substance having an attached labeling substance to an antibody. Then, the chromogenic substrate is oxidized by catalytic reaction of the labeling substance attached to the secondary probe substance, thereby producing an analyte comprising at least one or more of the labeling substance, the first oxide, or the second oxide. In the commercial immunoassay, 3,3',5,5'-tetramethylbenzidine (TMB) is mainly used for a chromogenic substrate when a chromogenic reaction is used, and lumino is mainly used for a luminescent substrate when a luminescent reaction is used. In this embodiment, the labeling substance may be horseradish peroxidase (HRP), and the chromogenic substrate may be 3,3',5,5'-tetramethylbenzidine (TMB).

In one embodiment, the target substance may be an antibody of anti-human immunodeficiency virus (HIV) or an antigen of human hepatitis B surface antigen (hHBsAg). An embodiment of the present invention may provide an immunoassay device having high measurement sensitivity, high reliability, and low measurement limits for the two types of diseases. Antigens such as the HIV and the hHBsAg cause diseases targeting humans, and accordingly, the present invention may provide a medical diagnostic device with high measurement sensitivity and high reliability.

The current measurer 300 contacts a silicon carbide (SiC) electrode at least partially doped with nitrogen(N) to the analyte, and measures a current of the analyte by applying a constant voltage. The current measurer 300 is as described above within a range that does not contradict. In addition, the concentration analyzer 400 analyzes the concentration of the target substance by using the measured current, which will be described in detail in the concentration analysis step (S700) of the target substance which will be described later.

Figure 7:
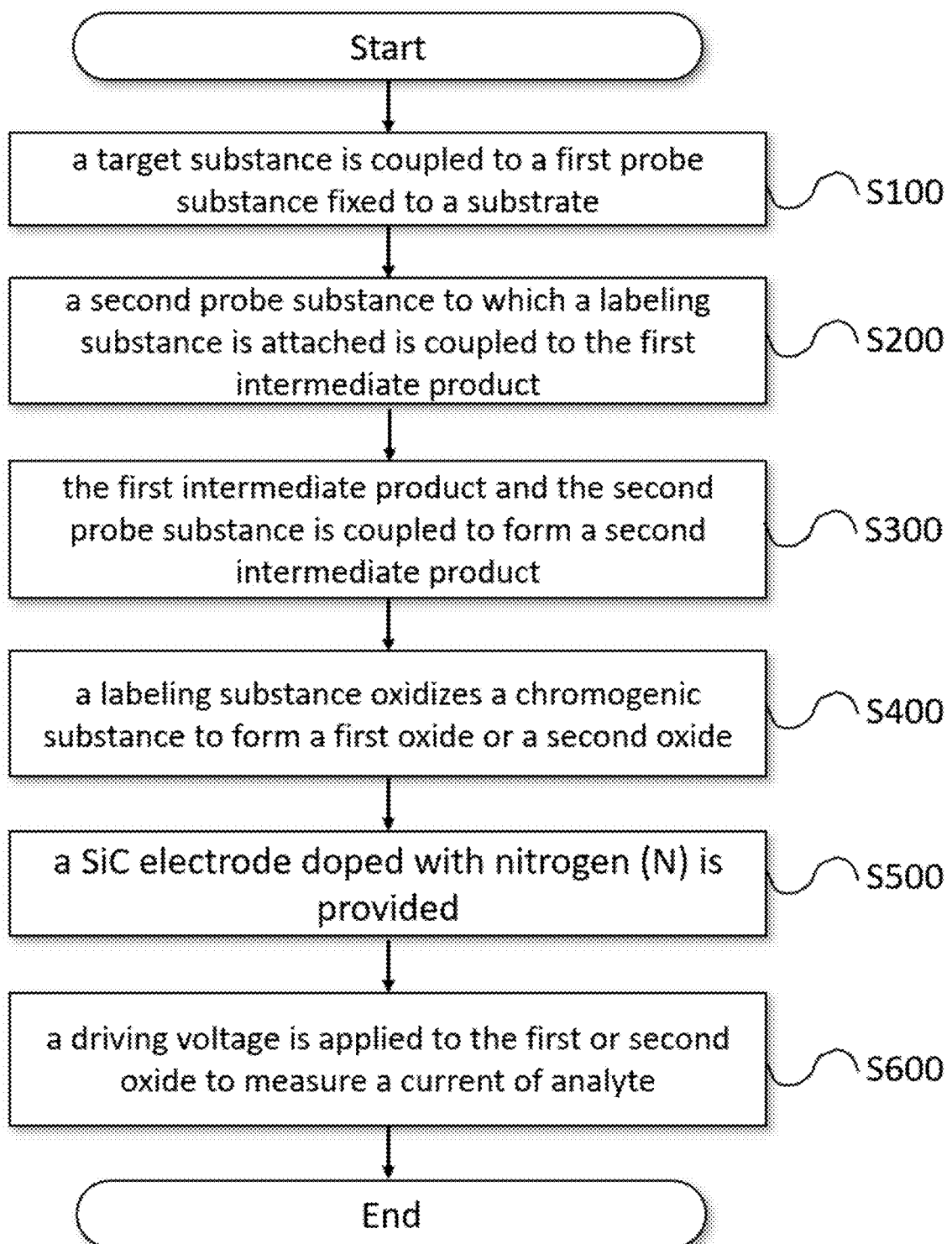
FIG. 7 is a flowchart showing an analysis method using an immunoassay apparatus.
Figure 8A:
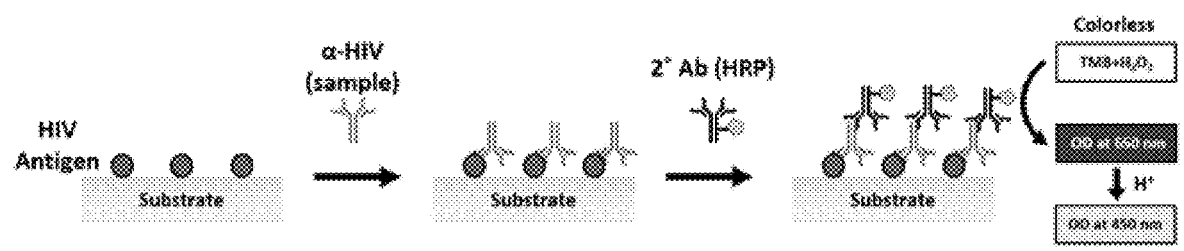
FIG. 8A is a schematic diagram of an immunoassay process for detecting an anti-human immunodeficiency virus (HIV) antibody.
Figure 8B:
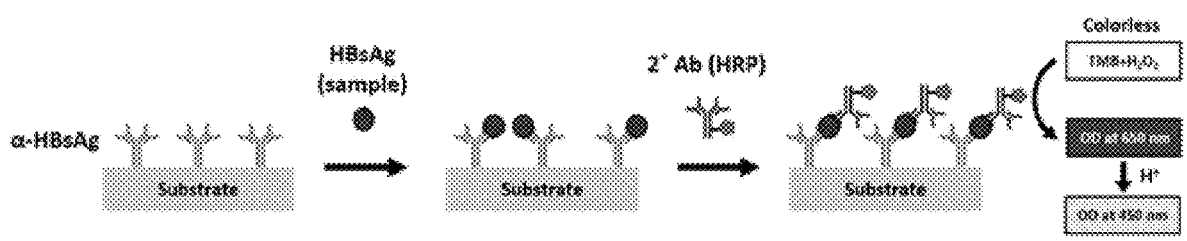
FIG. 8B is a schematic diagram of the immunoassay process for detecting the surface antigen of human hepatitis B surface antigen (hHBsAg)
Figure 8C:
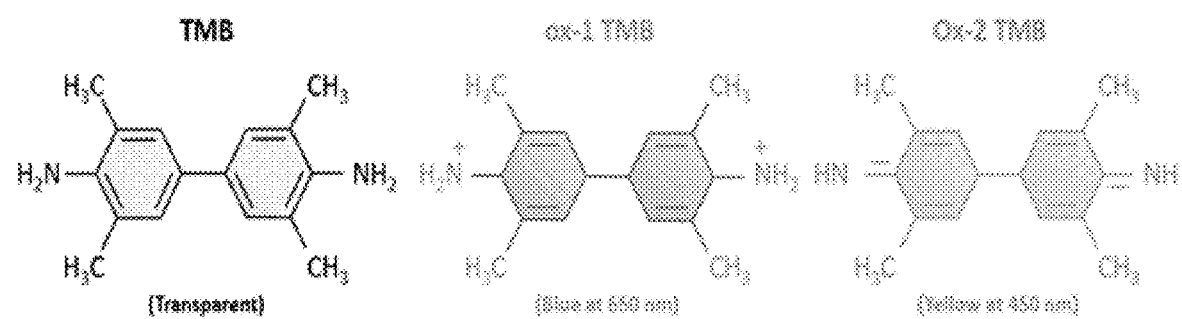
FIG. 8C is a structural formula according to the oxidation or reduction of tetramethylbenzidine (TMB) used as a chromogenic substrate in one embodiment.

Hereinafter, the method of immunoassay will be described in detail with reference to FIGS. 7 to 8C. FIG. 7 is a flowchart showing an analysis method using an immunoassay apparatus 2000, FIG. 8A is a schematic diagram of an immunoassay process for detecting an anti-human immunodeficiency virus (HIV) antibody, and FIG. 8B is a schematic diagram of the immunoassay process for detecting the surface antigen of human hepatitis B surface antigen (hHBsAg). However, this is only a preferred embodiment for achieving the object of the present invention, and of course, some steps may be added or deleted as necessary.

Referring to FIG. 7, in one embodiment, the immunoassay apparatus 2000 processes a target substance and then specifically couples the treated target substance to a substrate to which the primary probe substance is bound (S100). In one embodiment, referring to FIG. 8A, the primary probe substance may be an HIV antigen, and the target substance may be an HIV antibody. In addition, referring to FIG. 8B, in another embodiment, the primary probe substance may be an hHBsAg antibody, and the target substance may be an hHBsAg antigen. In another embodiment, the secondary probe substance may be a compound capable of coupling to the labeling substance, for example, anti-mouse immunoglobulin G (Anti-Mouse IgG-HRP) labeled with the HRP. The secondary antibody depends on the type of target substance to be detected, and may be of the same type as anti-goat, anti-mouse, or anti-human, and it may be of the same type as immunoglobulin G(igG), immunoglobulin M(igM), or immunoglobulin A(igA). The secondary probe substance may be various types of antibodies bound to the labeling substance. In addition, the labeling substance may be an oxidizing agent for dehydrogenating the substrate using hydrogen peroxide, and in one embodiment, the labeling substance may include peroxidase. For example, it may be an enzyme such as ascorbic acid or p-aminobenzoic acid cytochrome. In another embodiment, the labeling substance may include at least one or more of nanoparticles including a metal, a non-metal, an oxide of the metal or a non-metal, or a combination thereof, wherein the metal may include iron (Fe), gold (Au), Platinum (Pt) or inorganic nanoparticles serving as the peroxidase, and is not limited to a specific element.

Subsequently, the secondary probe substance to which the labeling substance is attached is processed to the first intermediate product to form a second intermediate product (S200), and the chromogenic substrate is oxidized by catalytic reaction of the labeling substance in the second intermediate product, so that a first oxide or a second oxide may be generated (S300). FIG. 8C is a structural formula according to the oxidation or reduction of tetramethylbenzidine (TMB) used as a chromogenic substrate in one embodiment. When a colorless TMB (transparent in FIG. 8C) is oxidized, a blue (650 nm) TMB(ox-1 TMB) is generated and when the ox-1 TMB is oxidized again, a yellow (450 nm) TMB(ox-2) is generated (S400). At this time, the ox-1 TMB is oxidized to ox-2 TMB at a rapid rate in acidic conditions. Therefore, the reduction reaction of ox-2 TMB may be easily measured. In this case, the chromogenic substrate may be transparent TMB, the first oxide may be ox-1 TMB, and the second oxide may be ox-2 TMB.

Thereafter, a silicon carbide (SiC) electrode doped with nitrogen (N) used for measuring a current signal generated from the electrochemical reaction between the chromogenic substrate, the first oxide and the second oxide is provided (S500), and the silicon carbide (SiC) electrode doped with nitrogen (N) is contacted to at least a portion of the first oxide or the second oxide, and a current signal of the analyte is measured by applying a constant voltage (S600). The detailed description of the structure, doping concentration, and measurement values of the surface capacitor of the silicon carbide (SiC) electrode doped with nitrogen(N) is as described above. The immunoassay method is an enzyme-linked immunosorbent assay (ELISA) method, and may be performed by a direct ELISA, an indirect ELISA, and a sandwich ELISA method.

In one embodiment, the current signal measurement may use chronoamperometry. Detailed description of the chronoamperometry is as described above. In other embodiment, the chronoamperometry may comprise a step for sequentially applying the reduction potential voltage and the oxidation potential voltage of the chromogenic substrate, a step for measuring the current over time, and a step for obtaining a result value from a difference between the current magnitude when the reduction potential voltage is applied, and the current magnitude when the oxidation potential voltage is applied. For example, when the chromogenic substrate is the TMB, the first oxide may be ox-1 TMB, and the second oxide may be ox-2 TMB.

Figure 9A:
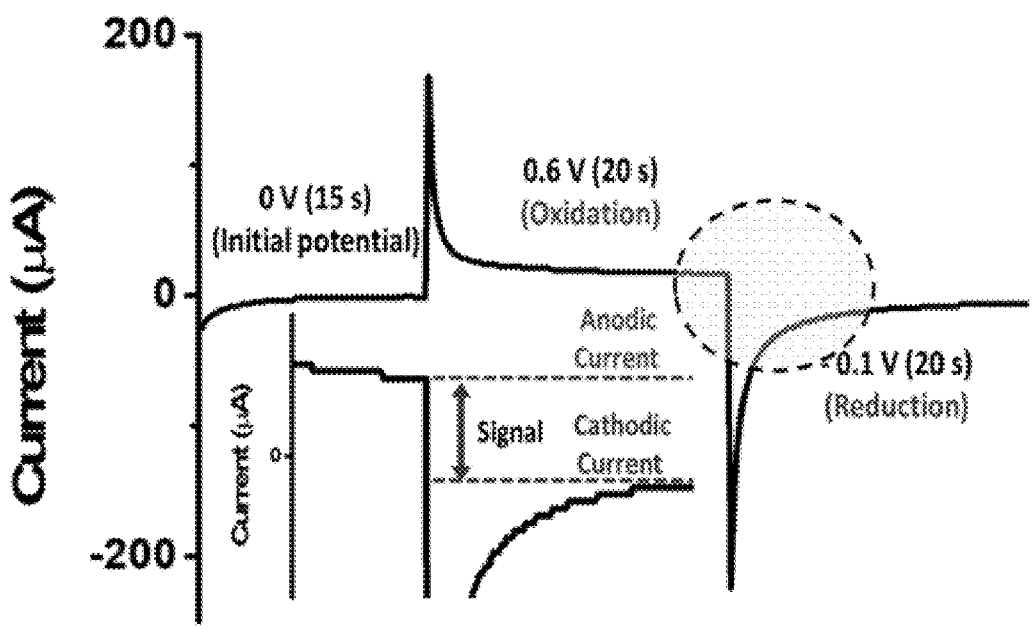
FIGS. 9A and 9B are graphs illustrating a chronoamperometry method for TMB analysis.
Figure 9B:
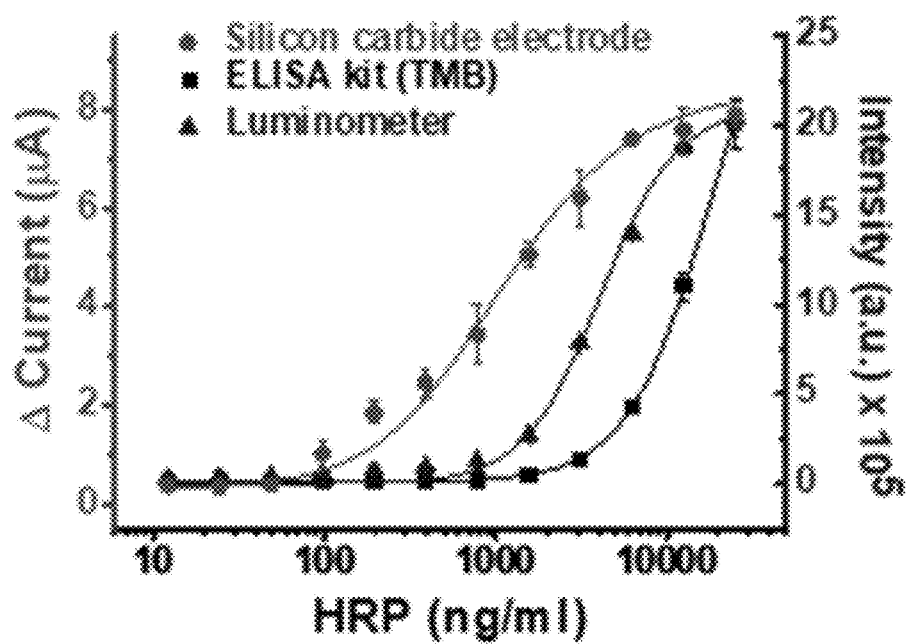

Thereafter, the concentration of the target substance is analyzed by using the measured current signal (S700). FIG. 9A and FIG. 9B are graphs illustrating a chronoamperometry method for TMB analysis. In one embodiment, the concentration of the target substance is analyzed by a difference in magnitude (signal=$I_{Red}$-$I_{Ox}$) between the current when the reduction potential is applied and the current when the oxidation potential is applied. For example, in the case of TMB, the oxidation potential is +600 mV, and the reduction potential is −1,000 mV. In this case, the average value of the magnitude difference of the current measured about 4 or more times may be used, and in the case of the measurement value using the ox-2 TMB, the linear constant ($R^2$) relative to the optical density was measured to be 0.99.

Figure 10A:
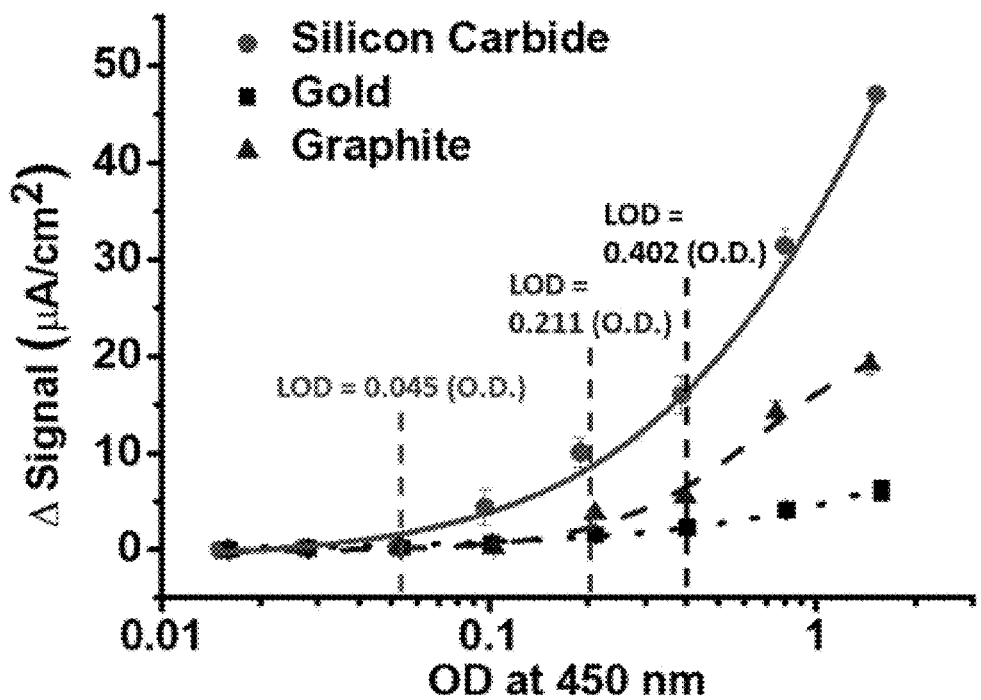
FIG. 10A is a graph comparing the TMB analysis results obtained by using the electrode, and the analysis results obtained by using the gold (Au) electrode and the carbon (Graphite) electrode.
Figure 10B:
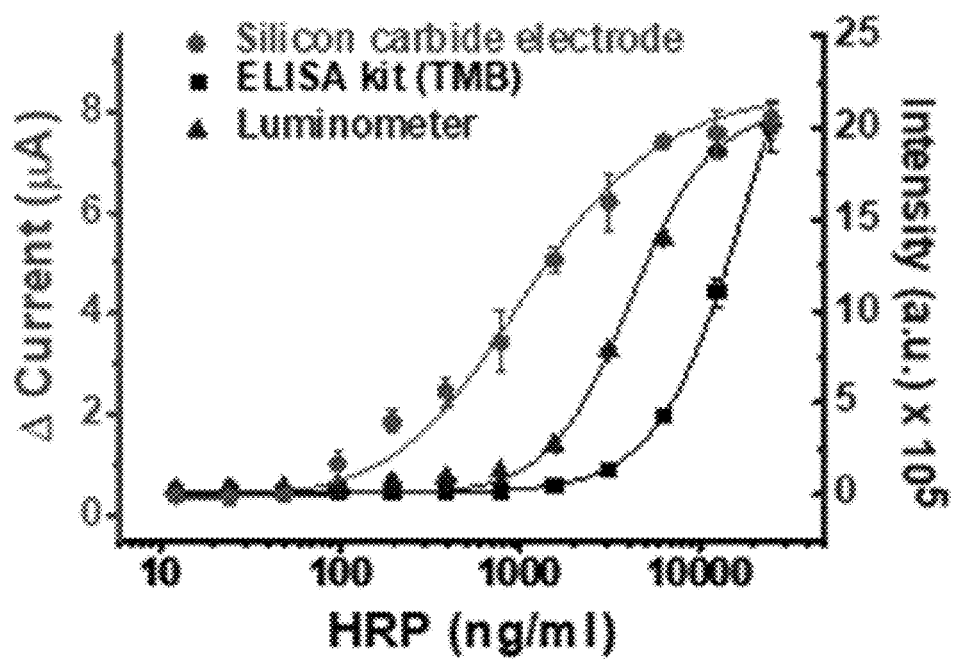
FIG. 10B is a graph in which the result of TMB analysis obtained by using chronoamperometry is compared with the luminescence analysis by luminor and the conventional TMB color development analysis.

FIG. 10A is a graph comparing the TMB analysis results obtained by using the electrode 10, and the analysis results of the gold (Au) electrode and the carbon (Graphite) electrode, and FIG. 10B is a graph in which the result of TMB analysis obtained by using chronoamperometry is compared with the luminescence analysis by luminor and the conventional TMB color development analysis.

Referring to FIG. 10A, it can be seen that the limit of detection (LOD) of the TMB analysis result using the electrode 10 is the lowest as 0.045. Referring to FIG. 10B, in one embodiment, under HRP conditions of various concentrations, the same concentration of TMB were treated for the same time to observe the sensitivity to the change in the HRP concentration.

It can be seen that the highest sensitivity is exhibited according to the change in the HRP concentration as a result of analyzing the TMB via the chronoamperometry. Therefore, as an embodiment of the present invention, when performing an immunoassay using the electrode 10 and the chronoamperometry, the highest measurement sensitivity, reliability, and low measurement limit may be obtained.

Figure 11A:
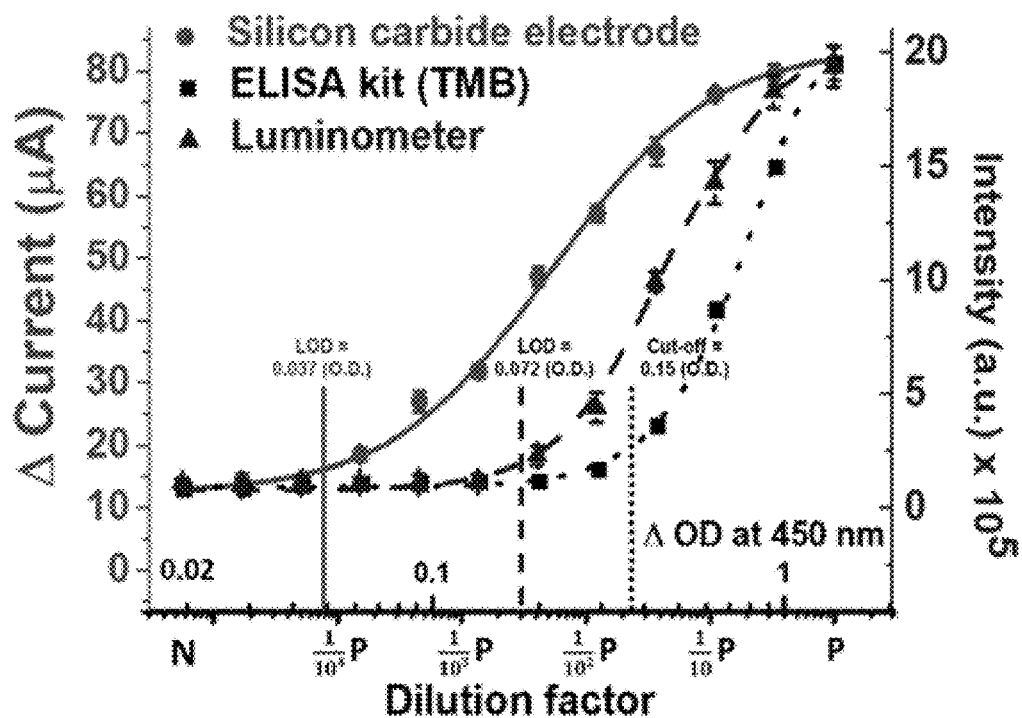
FIG. 11A is a graph comparing the respective result of concentration analysis of HIV antibodies obtained by chronoamperometry using electrodes, and a luminescence analysis by luminor and a conventional TMB color analysis.
Figure 11B:
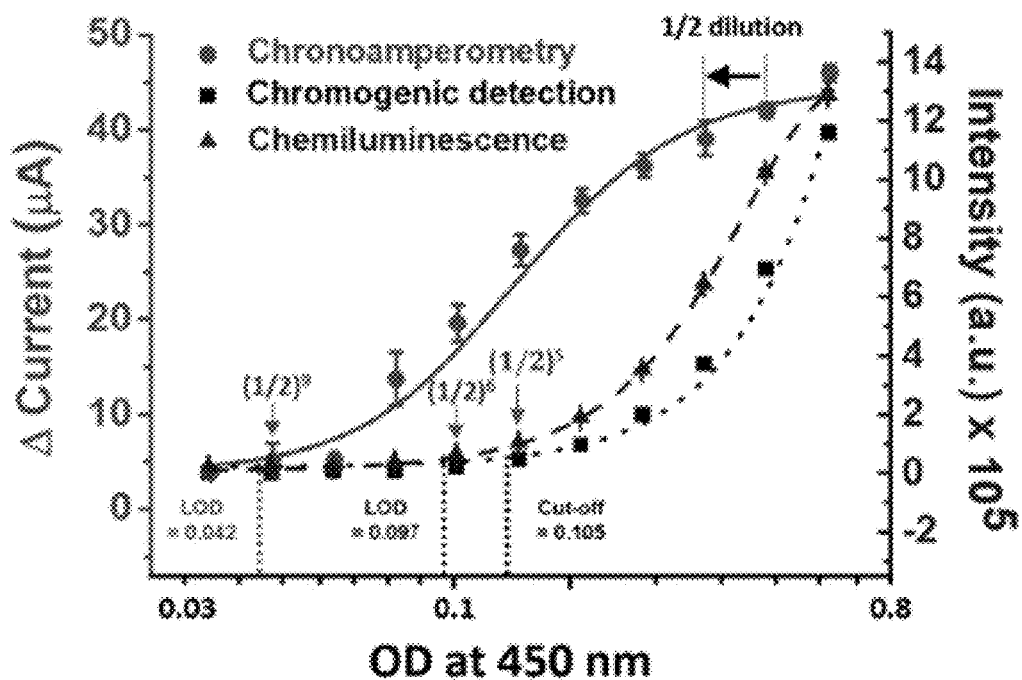
FIG. 11B is a graph comparing the result of concentration analysis of HIV antibodies obtained by chronoamperometry, and luminescence analysis using luminor and conventional TMB color development analysis.

FIG. 11A is a graph comparing the result of concentration analysis of HIV antibodies obtained by chronoamperometry using electrodes 10, and a luminescence analysis by luminor and a conventional TMB color analysis, and FIG. 11B is a graph comparing the result of concentration analysis of HIV antibodies obtained by chronoamperometry with an electrode 10, and luminescence analysis using luminor and conventional TMB color development analysis.

Referring to FIG. 11A, in one embodiment of the present invention, the measurement limit of the concentration analysis result of HIV antibody obtained by chronoamperometry using the electrode 10 is the lowest as 0.037 (based on optical density). Referring to FIG. 11B, similarly, in the embodiment of the present invention, it can be observed that the measurement limit of the concentration analysis result of hHBsAg antigen obtained by chronoamperometry using the electrode 10 is the lowest as 0.042 (based on optical density). Therefore, according to an embodiment of the present invention, when an analytical method performing chronoamperometry using an electrode 10 is employed, it is possible to implement a medical diagnostic kit and device having sensitivity of measurement and reliability which are remarkably higher level as compared with those of an optical analysis method, or an analysis method using chemiluminescence.

EXPLANATION OF NUMERICAL DENOTATIONS

10: a silicon carbide (SiC) electrode doped with nitrogen (N)
100: a high sensitive bio-quantification kit
SS: a substrate, WE: a working electrode, CE: a counter electrode, RA: a reaction area
1000: a high sensitive bio-quantification device
200: an immunoassayer
300: a current measurer
400: a concentration analyzer
2000: immunoassay device

What is claimed is:

1. A high-sensitivity bio-quantification kit comprising,
a substrate accommodating an analyte and providing at least one or more electrochemical reaction regions; and
a working electrode and a counter electrode arranged in the electrochemical reaction region to induce an electrochemical reaction of the analyte, and to detect a current change resulting from the electrochemical reaction,
wherein the working electrode includes silicon carbide doped at least partially with nitrogen (N).

2. A high-sensitivity bio-quantification device comprising,
a working electrode which is in contact with an analyte that generates a current signal by an electrochemical reaction, and includes silicon carbide (SiC) doped at least partially with nitrogen (N);
a counter electrode; and
a current measurer which applies a driving voltage between the working electrode and the counter electrode to induce an electrochemical reaction of the analyte and to measure a current generated by the electrochemical reaction, wherein the current measurer uses chronoamperometry.

3. A high-sensitivity bio-quantification device of the claim 2, wherein the chronoamperometry sequentially applies a reduction potential voltage and a oxidation potential voltage of the analyte, and measure the current over time.

4. An immunoassay device comprising,
an immunoassayer for generating an analyte, the analyte including at least one or more of a labeling substance, a first oxide, or a second oxide, wherein a first probe substance is fixed to a substrate, and a target substance targeted to be quantification is processed to selectively be bound to the fixed first probe substance, a second probe substance with a labeling substance attached thereto is processed to specifically be bound to an antibody, and a chromogenic substrate is oxidized due to a catalytic reaction of the labeling substance attached to the second probe substance;
a current measurer for contacting a silicon carbide (SiC) electrode doped at least partially with nitrogen (N) to the analyte, and for measuring a current of the analyte by applying a driving voltage; and
a concentration analyzer for analyzing a concentration of the target substance by using the measured current.

5. The immunoassay device of the claim 4, wherein the labeling substance includes at least one or more of peroxidase or nanoparticles containing a metal, a non-metal, or an oxide of the metal or the non-metal, or a combination thereof, and the metal includes iron (Fe), gold (Au), and platinum (Pt).

6. The immunoassay device of the claim 4, wherein the labeling substance is horseradish peroxidase (HRP), and the chromogenic substrate is 3,3',5,5'-tetramethylbenzidine (TMB).

7. The immunoassay device of the claim 4, wherein the target substance is an antibody of anti-human immunodeficiency virus (HIV) or an antigen of human hepatitis B surface antigen (hHBsAg).

8. An immunoassay method for measuring a concentration of a target substance, and comprising,
a step for forming a first intermediate product by processing a target substance and specifically coupling the processed target substance to a substrate to which a first probe substance is bound;
a step for forming a second intermediate product by binding a second probe substance to which a labeling substance is attached to the first intermediate product;
a step for generating a first oxide or a second oxide by oxidizing a chromogenic substrate according to a catalytic reaction of the labeling substance in the second intermediate product;
a step for providing a silicon carbide (SiC) electrode doped at least partially with nitrogen (N) used for measuring a current signal arising from an electrochemical reaction between the chromogenic substrate, the first oxide and the second oxide;
a step for contacting a silicon carbide (SiC) electrode doped at least partially with nitrogen (N) to the first oxide or the second oxide, and for applying a driving voltage to measure a current signal of analyte; and
a step for analyzing the concentration of the target substance using the measured current signal.

9. The immunoassay method of the claim 8, wherein the current signal measurement uses chronoamperometry.

10. The immunoassay method of the claim 9, wherein the chronoamperometry comprises,
a step of sequentially applying a reduction potential voltage and an oxidation potential voltage of the chromogenic substrate, and for measuring the current over time, and
a step for obtaining a result value from a difference between a current magnitude when the reduction potential voltage is applied, and a current magnitude when the oxidation potential voltage is applied.

11. The immunoassay method of the claim 8, wherein the labeling substance includes at least one or more of peroxidase, nanoparticles containing a metal, a non-metal, or an oxide of the metal or the non-metal, or a combination thereof, and the metal includes iron (Fe), gold (Au), and platinum (Pt).

12. The immunoassay method of the claim 8, wherein the labeling substance is horseradish peroxidase (HRP), the chromogenic substrate is 3,3',5,5'-tetramethylbenzidine (TMB).

13. The immunoassay method of the claim 8, wherein a measurement limit of an optical density of the target substance measured at 450 nm is greater than 0.37 and less than 0.042.

* * * * *